United States Patent [19]

Blackwood

[11] Patent Number: 4,580,576

[45] Date of Patent: Apr. 8, 1986

[54] ECG RECORDER

[75] Inventor: Roger A. Blackwood, High Wycombe, England

[73] Assignee: Chiltern International Limited, Buckinghamshire, United Kingdom

[21] Appl. No.: 571,589

[22] Filed: Jan. 17, 1984

[30] Foreign Application Priority Data

Jan. 20, 1983 [GB] United Kingdom ............... 8301488

[51] Int. Cl.<sup>4</sup> ............................................. A61B 5/04
[52] U.S. Cl. ..................................... 128/711; 128/696
[58] Field of Search ................ 200/51.09, 51.1, 51.11; 128/639–640, 644, 695–696, 709–710, 908, 711

[56] References Cited

U.S. PATENT DOCUMENTS

| 409,437 | 8/1889 | Vernette | 128/791 |
|---|---|---|---|
| 2,611,368 | 9/1952 | Pecora | 128/644 |
| 3,067,749 | 12/1962 | Walters | 128/644 |
| 3,229,687 | 1/1966 | Holter et al. | 128/711 |
| 3,280,270 | 10/1966 | Allington | 128/711 |
| 3,865,101 | 2/1975 | Saper et al. | 128/696 |
| 3,913,567 | 10/1975 | Streckmann | 128/711 |
| 3,922,686 | 11/1975 | France et al. | 128/696 |
| 4,051,842 | 10/1977 | Hazel et al. | 128/710 |
| 4,129,128 | 12/1978 | Thalmann | 128/690 |
| 4,211,238 | 7/1980 | Shu et al. | 128/711 |
| 4,337,383 | 6/1982 | Daigaku | 200/51.1 |
| 4,380,691 | 4/1983 | Sato | 200/51.1 |

Primary Examiner—William E. Kamm
Assistant Examiner—Mitchell J. Shein

[57] ABSTRACT

An ECG recorder apparatus includes a recorder and a lead arrangement comprising a pair of manually operable resiliently biased jaws carrying electrodes. The electrodes are connected via a connection and a lead to a jack plug which on insertion in the corresponding socket in the recorder causes the recorder to commence operation. The apparatus may be applied by a patient to record an ECG when symptoms are perceived. The electrode arrangement may be easily and reliably applied and the fact that the recorder begins operating automatically reduces the possibility of patient error.

1 Claim, 3 Drawing Figures

ECG RECORDER

BACKGROUND OF THE INVENTION

The invention relates to ECG recorders, and in particular to recorders adapted to be used by a patient to record his or her own cardiac activity.

It has been found that in patients suffering from intermittent occurrences of abnormal cardiac acitivity it is difficult to obtain a recording of the elecrocardiogram of the abnormal activity because of the uncertainty as to when this will occur. For example, a patient may feel symptoms which recur at unpredictable times and at intervals of several days or more. It is desirable to examine the electrocardiogram during these symptoms for diagnostic purposes. It is of course possible to arrange for the patient to stay in hospital and be permanently connected to a cardiac monitoring apparatus. However, this is expensive and there is no guarantee that the symptoms will recur within a reasonable time. Further, a considerable amount of data will be collected which contains no useful information and it is very time consuming and expensive to scan long periods of a normal ECG whilst searching for abnormal activity. A further disadvantage of long-term monitoring is that the patient electrode contact deteriorates and has to be renewed to avoid poor results.

Ambulatory monitors have been proposed, e.g. the so-called "24 hour monitor". Although these are less expensive to use than the cost of hospital monitoring, they have the same disadvantages associated with long-term monitoring. An ambulatory monitor has been described which employs chest electrodes which the patient is expected to apply when feeling symptoms. However, relatively involved procedures have to be followed to apply the electrodes and start the recorder, and the patient may fail to follow the procedures correctly or may not be able to carry out the procedures before the symptoms vanish. Means have to be provided in the monitor to indicate the correct connection of the electrode and proper operation of the recorder.

To facilitate setting up of the system by the patient it is desirable that the electrode arrangement should be as simple as possible, and should permit easy application by the patient. Hitherto, electrode arrangements for cardiac monitoring have comprised one or more electrodes which are applied to the patient's chest, e.g. by adhesive tape. The application of such electrodes requires the patient to partially undress, and in order to ensure good adhesion and good contact the area to which the electrodes are to be applied must be shaved and swabbed using surgical spirit or similar. The application of such electrodes takes time, during which relevant information may be lost, and also provides opportunity for patient error.

SUMMARY OF THE INVENTION

An object of the present invention is to overcome the above problems by providing an ECG recorder apparatus which is readily portable and which may be set up by the patient in the least possible time with the minimum of preparation and minimum likelihood of patient error leading to erroneous results or malfunctioning of the equipment.

A further object is to provide an ECG recorder having an electrode arrangement adapted to be applied quickly by the patient to his or her body with the minimum of preparation.

In accordance with the present invention an ECG recorder apparatus comprises a recorder, an electrode arrangement adapted to be applied by a patient to appropriate body sites, the electrode arrangement comprising a plurality of manually operable resiliently biased jaws and each of the jaws being provided with electrode means adapted to make electrical contact with that portion of the patient's body to which the jaws are applied, and means for automatically activating the recorder when the electrode arrangement is connected thereto.

The apparatus of the invention has the advantage of eliminating the possibility of loss of relevant information by the patient neglecting to switch on the recorder after connecting the electrodes.

Generally, the electrode arrangement will comprise a pair of electrodes provided with a lead arrangement terminating in means adapted for connection to the recorder. Preferably the lead arrangement terminates in a plug and the recorder is provided with a corresponding socket, the socket incorporating a switch which activates the recorder when the plug is inserted in the socket. For example, the plug may be a jack plug arranged on insertion into the socket to connect a battery to electrical circuitry of the recorder.

The jaws will generally be applied to the patient's limbs. In a preferred aspect two pairs of jaws are provided, each preferably having a pair of electrodes, one mounted on each arm of the jaws. The jaws may respectively be connected for example to an arm and a leg of the patient. No preliminary swabbing is normally necessary. This means that the patient can apply the electrodes very quickly, and they will remain firmly in place without the need for an adhesive. Because the jaws are applied to the limbs there is no need for the patient to undress before taking the recording.

Thus the invention provides a recording apparatus which is very simple to operate and which can be used safely by the patient.

The novel features of the invention are set forth with particularity in the appended claims. The invention will best be understood from the following description when read in conjunction with the accompanying drawings.

DESCRIPTION OF PREFERRED EMBODIMENT

Figure 1:
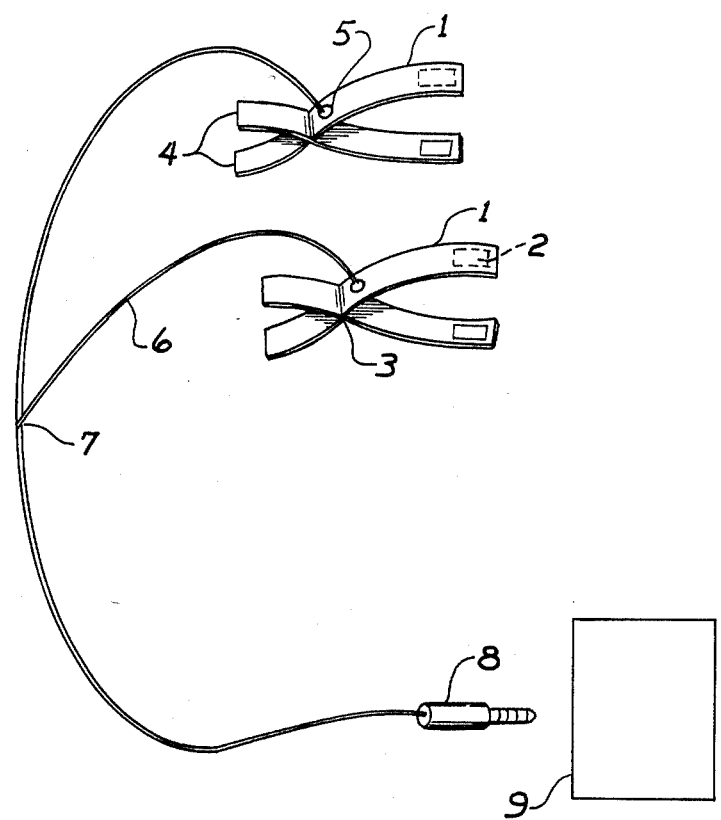
FIG. 1 is a representation (not to scale) of recorder apparatus according to the invention.

In FIG. 1, two pairs of jaws, indicated generally by 1, are each provided with a pair of electrodes 2. The jaws are hinged at 3 and biased such that the ends bearing the electrodes are urged towards one another. The jaws may be opened by manually urging together the opposite ends of the jaws indicated by 4. Conveniently the jaws are constructed of plastics material, the resilient biasing being built into their construction or provided by resilient means acting in the region of the hinge 3. Each pair of electrodes is provided with a contact 5 to which the lead 6 is attached. The connection is preferably a soldered and riveted or other firm connection which will resist disconnection in use. The jaws are so designed that a single contact 5 receives the input from both electrodes 2. The leads from the jaws are run separately for about 1 meter so as to permit the application of the jaws to body sites (e.g. arm and leg) spaced apart from one another. The leads may then run together from point 7, terminating in a jack plug 8 which is adapted to be inserted in the socket of the recorder 9.

Figure 2:
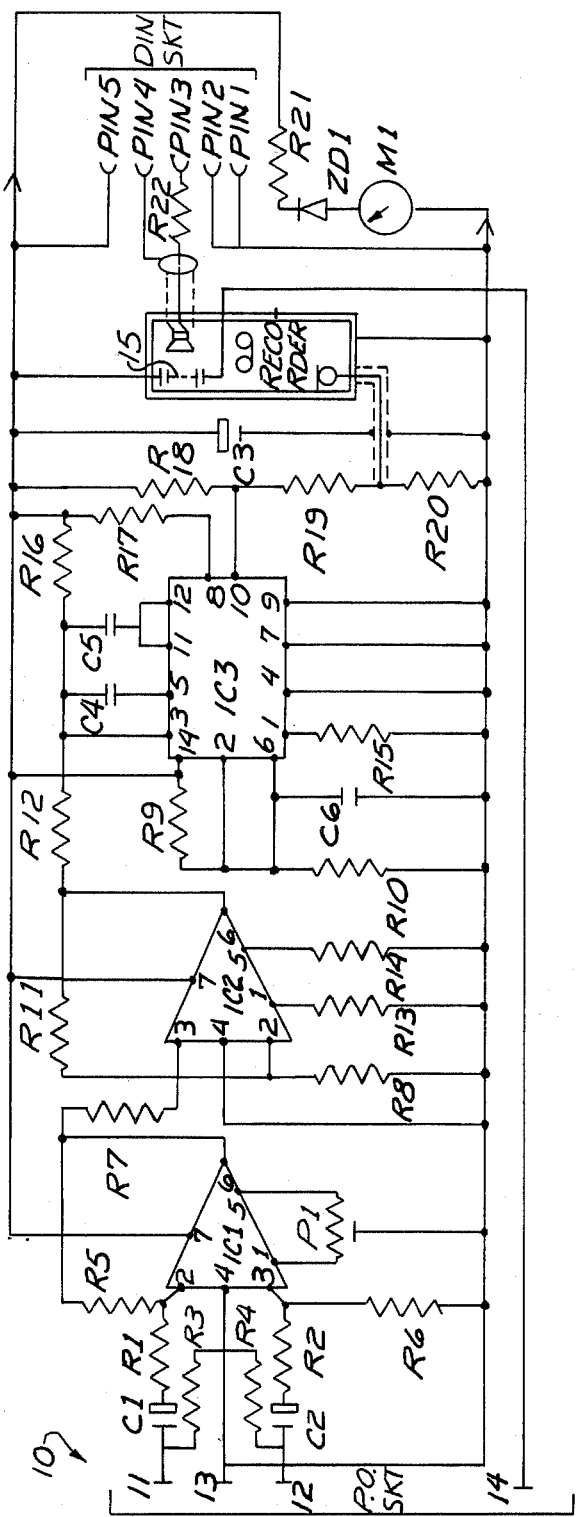
FIG. 2 is a circuit diagram of the recorder.

FIG. 2 shows a circuit diagram of part of the recorder 9, which may for example be a Philips LFH0590 recorder with the additional circuitry shown in FIG. 2. A jack-type socket 10 is shown schematically at the left-hand side of FIG. 2; the terminals 11 and 12 of socket 10 are arranged to be connected to the electrodes 2 of the patient leads and the terminal 13 is a common point of the circuit. The terminal 14 is connected to the negative terminal of the battery 15 of the recorder. The plug 8 and socket 10 cooperate such that when the plug is inserted in the socket the terminals 13 and 14 are interconnected thereby supplying power to the circuit of FIG. 2 by means of completing a path for current flow between terminal 14 and the common or ground point of the circuit. The plug 8 may interconnect the terminals 13 and 14 by virtue of both terminals contacting the same conductive part of the plug, or alternatively one of the contacts 13 and 14 may be movable and arranged to be moved to contact the other by the plug when it is inserted.

In FIG. 2 IC1 is an integrated differential amplifier for amplifying the electrocardiac signals presented to terminals 11 and 12. This is followed by a further amplifier IC2 and by a voltage-to-frequency converter circuit IC3. The output of circuit IC3 is supplied to the microphone input terminal of the recorder. A small meter M1 and Zener diode ZD1 are provided to monitor the battery voltage.

Specifically, the input electrocardiac signals are coupled by capacitors C1 and C2 and resistors R1 and R2 to the inputs of amplifier IC1. Resistors R3-R6 and potentiometer P1 set the d.c. conditions. The output of amplifier IC1 is coupled via resistor R7 to the input of amplifier IC2. Resistors R11 and R8 provide feedback and resistors R13 and R14 provide the biasing conditions. The output of amplifier IC2 is supplied via resistor R12 to voltage-to-frequency converter IC3 and resistors R9, R10, R15-R18 and capacitors C4-C6 are biasing and frequency determining components. The output is supplied to the recorder input via potential divider R18-R20. The power supply is decoupled by capacitor C3. Resistor R22 is an output resistor. Suitable component values are:

| R1 | 51k | R2 | 51k | R3 | 120k |
|---|---|---|---|---|---|
| R4 | 120k | R5 | 820k | R6 | 820k |
| R7 | 10k | R8 | 10k | R9 | 10k |
| R10 | 10k | R11 | 620k | R12 | 1 M |
| R13 | 6k2 | R14 | 6k8 | R15 | 100k |
| R16 | 1 M | R17 | 10k | R18 | 10k |
| R19 | 68k | R20 | 33k | R21 | 1k |
| R22 | 820 ohms | VR1 | 10k Present | | |
| C1 | 2.2 μF Tantalum | | | C2 | 2.2 μF Tantalum |
| C3 | 100 μF Tantalum | | | C4 | 150 pF Ceramic |
| C5 | 680 pF Polyester | | | C6 | 1000 pF Ceramic |
| IC1 | 3140 | IC2 | 3140 | IC3 | 8114 |
| M1 | 0.5 mA fsd | ZD1 | 6.8 V Zener diode | | |

Figure 3:
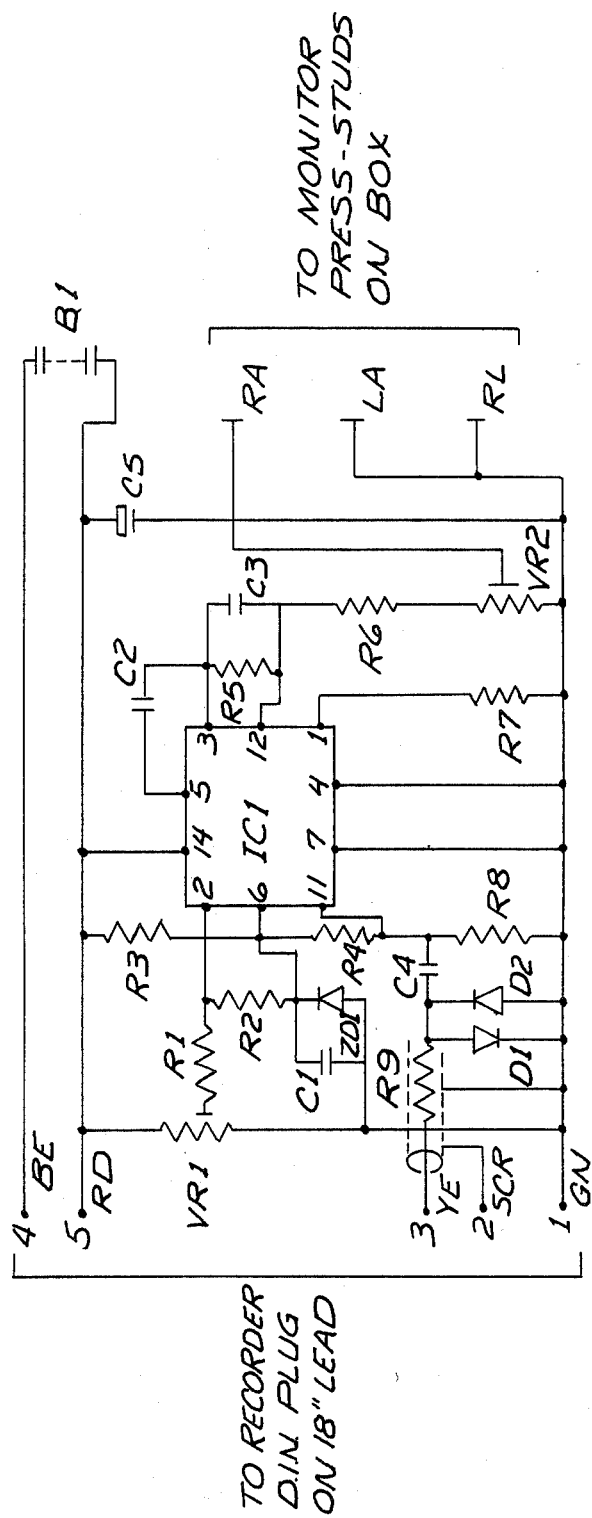
FIG. 3 is a circuit diagram of a decoder for reproducing a recorded ECG.

FIG. 3 shows a decoder unit for recovering the ECG signal. The recorder is replayed and the output is supplied to terminal 3 in FIG. 3 and via resistor R9 and capacitor C4 to a frequency-to-voltage converter IC1. The output of the frequency-to-voltage converter is connected to press-stud terminals via a variable resistor VR2. A conventional ECG monitor may be connected to the press-studs as if they were patient electrodes. Diodes D1 and D2 provide input protection and resistors R1-R8, potentiometer VR1 and VR2 and capacitors C1-C3 are biasing and timing components. Suitable component values are:

| R1 | 470k | R2 | 10k | R3 | 1.8k |
|---|---|---|---|---|---|
| R4 | 1 M | R5 | 1 M | R6 | 1 M |
| R7 | 100k | R8 | 10 M | R9 | 220 ohms |
| VR1 | 100k Preset | VR2 | 22k Preset | C3 | 1000 pF |
| C1 | 1000 pf | C2 | 47 pF | ZD1 | 4.7 V Zener |
| C4 | 0.04 μF | C5 | 22 μF Tant | | |
| D1 | 1N4008 | D2 | 1N4001 | | |
| IC1 | 8114 | | | | |

Although a particular embodiment of the invention has been described and illustrated herein, it is recognized that modifications and variations may readily occur to those skilled in the art. Consequently it is intended that the claims be interpreted to cover such modifications and variations.

What is claimed is:

1. A portable ECG data collection and storage apparatus comprising:

recorder means for recording data in a data storage medium, said recorder means being electrically operated and normally in an unenergized state, said recorder means including:

a source of operating current, socket means having at least a pair electrically isolated data input terminals and a pair of further electrically isolated current supply terminals, the establishment of a short circuit between said current supply terminals causing energization of said recorder means whereby data may be recorded in the storage medium, differential amplifier means connected to said socket means data input terminals for providing output signals commensurate with the differences between the potentials applied to a pair of input terminals of said amplifier means, said differential amplifier means input terminals being connected to respective of said socket means data input terminals, voltage-to-frequency converter means for receiving the signals provided by said amplifier means and providing a variable frequency output signal commensurate therewith, means for recording said variable frequency output signals in said data storage medium, and output terminal means, the recorded variable frequency signals appearing at said output terminal means upon playback of said recording means;

electrode means adapted for self-application by a patient to an extremity of his body, said electrode means comprising at least two pairs of manually operable jaws, the jaws of each of said pairs being pivotally interconnected and being resiliently biased toward one another, said jaws being operable against said resilient bias to open to a degree necessary to receive therebetween an extremity of the patient, at least one of said jaws of each pair being provided with an electrode configured to establish electrical contact with the surface of an extremity of the patient's body disposed between the jaws of the pair;

plug means, said plug means being complementary to said recorder means socket means whereby insertion of said plug means into said socket means will establish substantially a short circuit between said current supply terminals whereby said recorder means be energized from said source of operating current, said plug means additionally including at least a pair of electrically isolated data supply terminals which will be electrically connected to said recorder means socket data input terminals upon insertion of said plug means into said socket means;

flexible conductor means for connecting an electrode on each of said pairs of jaws to one of said plug means data supply terminals; and decoder means, said decoder means converting said recorded variable frequency signals to electrical potentials for inputting to an electrocardiographic recording apparatus for producing a record thereof which may be visually examined.

* * * * *